United States Patent [19]

Kluge

[11] 4,051,150

[45] Sept. 27, 1977

[54] 3-(2-DIALKYLAMINO-2-DIALKYLPHOSPHONYLVINYL)-6,11-DIHYDRODIBENZO-[b.e.]-THIEPIN-11-ONE

[75] Inventor: Arthur F. Kluge, Los Altos, Calif.

[73] Assignee: Syntex (U.S.A.) Inc., Palo Alto, Calif.

[21] Appl. No.: 697,652

[22] Filed: June 18, 1976

[51] Int. Cl.² .......................................... C07D 337/12
[52] U.S. Cl. ................................................ 260/327 B
[58] Field of Search ............... 260/327 B, 333, 515 R, 260/517, 945, 968

[56] References Cited

PUBLICATIONS

Gross, et al., Angew. Chem. Internat. Ed., vol. 7 (1968), No. 5, pp. 391–392.

*Primary Examiner*—Cecilia M. S. Jaisle
*Attorney, Agent, or Firm*—Gerard A. Blaufarb; William B. Walker

[57] ABSTRACT

This invention relates to a novel method for the preparation of 6,11-dihydrodibenzo-[b.e.]-thiepin-11-one-3-acetic acid and the novel intermediates 3-(2-dialkylamino-2-dialkylphosphonylvinyl)-6,11-dihydrodibenzo-[b.e.]-thiepin-11-one in the preparation thereof.

2 Claims, No Drawings

3-(2-DIALKYLAMINO-2-DIALKYLPHOSPHONYL-VINYL)-6,11-DIHYDRODIBENZO-[b.e.]-THIEPIN-11-ONE

This invention relates to a novel method for the preparation of 6,11-dihydrodibenzo-[b.e.]-thiepin-11-one-3-acetic acid, disclosed in copending application U.S. application Ser. No. 643,086, filed Nov. 21, 1975, and to the novel intermediates 3-(2-dialkylamino-2-dialkyl-phosphonylvinyl)-6,11-dihydrodibenzo-[b.e.]-thiepin-11-one (II) in the preparation thereof, according to the following reaction sequence:

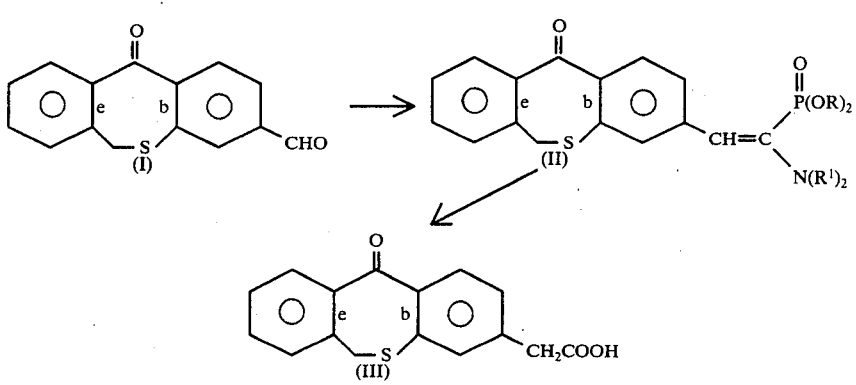

wherein R and $R^1$ represent an alkyl radical containing from 1 to 4 carbon atoms, e.g., methyl, ethyl, propyl, butyl, and the like.

The compound of formula (I), 6,11-dihydrodibenzo-[b.e.]-thiepin-11-one-3-carboxaldehyde, disclosed in copending U.S. application Ser. No. 697,648, filed on even date herewith, is treated with a tetraalkyl dialkylaminomethylenediphosphonate alkali metal salt reagent, in the presence of an inert organic solvent, e.g., dioxane, 1,2-dimethoxyethane, tetrahydrofuran, and the like, at a temperature of from about 0° to about 100° C, for from about 10 minutes to about 2 hours, preferably from about 20° to 60° C for from about 1 to about 2 hours, to obtain a novel non-pharmaceutical compound of Formula (II), 3-(2-dialkylamino-2-dialkylphosphonylvinyl)-6,11-dihydrodibenzo-[b.e.]-thiepin-11-one.

The tetraalkyl dialkylaminomethylene diphosphonate alkali metal salt reagent is prepared by adding a tetraalkyl dialkylaminodiphosphonate [prepared as described in Angew. Chem. Internat. Ed. 7,391 (1968)] to an alkali metal hydride, e.g., sodium hydride, potassium hydride or lithium hydride, in an inert organic solvent, e.g., dioxane, 1,2-dimethoxyethane, tetrahydrofuran, and the like.

Representative of the tetraalkyl dialkylaminomethylenediphosphonate alkali metal salt reagents which can be used to prepare the compounds of Formula (II) are
tetraethyl dimethylaminomethylenediphosphonate sodium salt,
tetramethyl dimethylaminomethylenediphosphonate sodium salt,
tetramethyl diethylaminomethylenediphosphonate sodium salt,
tetraethyl diethylaminomethylenediphosphonate sodium salt,
tetraethyl dipropylaminomethylenediphosphonate sodium salt,
tetraethyl dibutylaminomethylenediphosphonate sodium salt,
tetrapropyl dimethylaminomethylenediphosphonate sodium salt,
tetrabutyl dimethylaminomethylenediphosphonate sodium salt,
tetrapropyl dipropylaminomethylenediphosphonate sodium salt,
or the potassium or lithium salt reagents corresponding thereto, and the like, with tetraethyl dimethylaminomethylenediphosphonate sodium salt reagent being preferred.

The novel compounds of formula (II) are then hydrolyzed in the presence of an aqueous acid, e.g., hydrochloric acid, sulfuric acid, perchloric acid, and the like, at a temperature of from about 50° to about 100° C, for from about 1 to 3 hours, preferably from about 60° to 70° C, for from about 1 to 2 hours, to yield the compound of Formula (III), 6,11-dihydrodibenzo-[b.e.]-thiepin-11-one-3-acetic acid.

It is to be understood that isolation of the compounds described herein can be effected, if desired, by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the Examples herein below. However, other equivalent separation or isolation procedures could, of course, also be used.

By the term room temperature is meant a temperature of from about 15° to about 25° C.

A further understanding of the invention can be had from the following non-limiting Preparation and Examples.

PREPARATION

3 G. of tetraethyl dimethylaminomethylenediphosphonate [prepared as described in Angew. Chem. Internat. Ed. 7,391 (1968)] is stirred overnight at room temperature with 200 mg. of 100% sodium hydride in 15 ml of dioxane to yield a tetraethyl dimethylaminomethylenediphosphonate sodium salt reagent solution which is used, without further treatment, in Example 1.

EXAMPLE 1

To 2.5 ml. of the tetraethyl dimethylaminomethylenediphosphonate sodium salt reagent solution in 5 ml. of dioxane solution, prepared in the Preparation above, there is added 250 mg. of 6,11-dihydrodibenzo-[b.e.]-thiepin-11-one-3-carboxaldehyde (I) in 5 ml. of dioxane and the reaction mixture is stirred at 60° C for 1 hour, the completeness of the reaction being determined by thin-layer chromatography, to yield a solution which is poured into 100 ml. of water and extracted with 50 ml. of ethyl acetate solution. The ethyl acetate solution extract is washed with 20 ml. of water and 20 ml. of saturated sodium chloride solution, dried over sodium sulfate and evaporated under vacuum to yield an oily residue of 3-(2-dimethylamino-2-diethylphosphonylvinyl)-6,11-dihydrodibenzo-[b.e.]-thiepin-11-one (II; R = ethyl, R$^1$ = methyl).

In like manner, there are obtained other 3-(2-dialkylamino-2-dialkylphosphonylvinyl)-6,11-dihydrodibenzo-[b.e.]-thiepin-11-ones.

EXAMPLE 2

To the oily residue of 3-(2-dimethylamino-2-diethylphosphonylvinyl)-6,11-dihydrodibenzo-[b.e.]-thiepin-11-one (II; R = ethyl; R$^1$ = methyl) there is added 15 ml. of concentrated hydrochloric acid and the thus obtained reaction mixture is stirred at 70° C for 1 hour, the completeness of the reaction being determined by thin-layer chromatography. The reaction mixture is poured into 100 ml of water and extracted with 50 ml. of ethyl acetate. The ethyl acetate extract is washed with 20 ml. of water, 20 ml. of saturated sodium chloride solution, dried over sodium sulfate to yield a residue which is crystallized from diethyl ether to yield about 120 mg of yellow crystals of 6,11-dihydrodibenzo-[b.e.]-thiepin-11-one-3-acetic (III), which is recrystallized from 5 ml. of benzene to yield 90 mg of crystalline 6,11-dihydrodibenzo-[b.e.]-thiepin-11-one-3-acetic acid (III) having a melting point of 150°–155° C.

In like manner, substituting other 3-(dialkylamino-2-dialkylphosphonylvinyl)-6,11-dihydrodibenzo-[b.e.]-thiepin-11-one for 3-(2-dimethylamino-2-diethylphosphonylvinyl)-6,11-dihydrodibenzo-[b.e.]-thiepin-11-one and/or other acids for hydrochloric acid is productive of 6,11-dihydrodibenzo-[b.e.]-thiepin-11-one-3-acetic acid.

What is claimed is:

1. A compound of the formula:

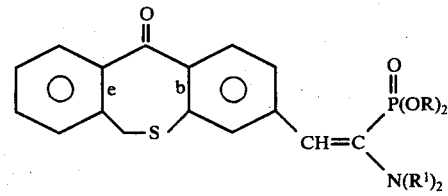

wherein R and R$^1$ represent an alkyl radical containing from 1 to 4 carbon atoms.

2. The compound of claim 1 in which R is ethyl and R$^1$ is methyl, 3-(2-dimethylamino-2-diethylphosphonylvinyl)-6,11-dihydrodibenzo-[b.e.]-thiepin-11-one.

* * * * *